(12) United States Patent
Sworski et al.

(10) Patent No.: US 10,473,009 B2
(45) Date of Patent: Nov. 12, 2019

(54) SYSTEM AND METHOD FOR PREDICTING REMAINING OIL LIFE IN VEHICLES

(71) Applicant: Valvoline Licensing and Intellectual Property, LLC, Lexington, KY (US)

(72) Inventors: Adam E. Sworski, Catlettsburg, KY (US); Kyla Grace Brooks, Montreal (CA); Matthew A. Lechleiter, Lexington, KY (US); Frances E. Lockwood, Georgetown, KY (US)

(73) Assignee: Vavoline Licensing and Intellectual Property LLC, Lexington, KY (US)

( * ) Notice: Subject to any disclaimer, the term of this patent is extended or adjusted under 35 U.S.C. 154(b) by 102 days.

(21) Appl. No.: 15/874,024

(22) Filed: Jan. 18, 2018

(65) Prior Publication Data

US 2018/0202333 A1    Jul. 19, 2018

Related U.S. Application Data

(60) Provisional application No. 62/447,545, filed on Jan. 18, 2017.

(51) Int. Cl.
*F01M 11/00* (2006.01)
*F01M 11/12* (2006.01)
*G01N 25/72* (2006.01)
*G01N 33/28* (2006.01)
*G01F 23/00* (2006.01)
(Continued)

(52) U.S. Cl.
CPC ............. *F01M 11/12* (2013.01); *G01F 23/00* (2013.01); *G01K 13/02* (2013.01); *G01N 25/72* (2013.01); *G01N 33/2888* (2013.01);

*G07C 5/008* (2013.01); *F01M 2011/142* (2013.01); *F01M 2011/1473* (2013.01)

(58) Field of Classification Search
CPC ............. F01M 11/12; F01M 2011/142; F01M 2011/1453; F01M 2011/1473; F01M 2011/1486; F01M 2011/1493
See application file for complete search history.

(56) References Cited

U.S. PATENT DOCUMENTS 4,677,847 A * 7/1987 Sawatari ............ G01N 33/2888
73/114.55
4,862,393 A   8/1989 Reid et al.
(Continued)

FOREIGN PATENT DOCUMENTS

EP    1308666 A2    7/2003

OTHER PUBLICATIONS

PCT Notification of Transmittal of the International Search Report and the Written Opinion of the International Searching Authority, or the Declaration regarding related PCT Application No. PCT/US2018/014139; dated Apr. 26, 2018; 2 pages.
(Continued)

*Primary Examiner* — Thomas N Moulis
(74) *Attorney, Agent, or Firm* — Benesch, Friedlander, Coplan & Aronoff LLP

(57) ABSTRACT

Systems and methods are described for predicting a remaining oil life in an engine of a vehicle. One or more parameters of the engine can be monitored over a period of time. A hot compartment temperature can be determined from the parameter. A condition of the oil can be determined based on the hot compartment temperature, and the condition of the oil can be displayed.

22 Claims, 5 Drawing Sheets

(51) Int. Cl.
*G07C 5/00* (2006.01)
*G01K 13/02* (2006.01)
*F01M 11/10* (2006.01)

(56) References Cited

U.S. PATENT DOCUMENTS

| | | | |
|---|---|---|---|
| 5,633,796 A | 5/1997 | Cullen et al. | |
| 5,749,339 A * | 5/1998 | Graham | F01M 11/0458 123/73 AD |
| 5,750,887 A * | 5/1998 | Schricker | F01M 11/10 340/438 |
| 5,970,942 A * | 10/1999 | Koeberlein | F01M 11/0458 123/196 R |
| 6,055,470 A * | 4/2000 | Londot | G01M 15/042 701/33.4 |
| 6,213,080 B1 * | 4/2001 | Marsh | F01M 11/0458 123/196 R |
| 6,253,601 B1 * | 7/2001 | Wang | F01M 11/10 340/438 |
| 6,741,938 B2 | 5/2004 | Berndorfer | |
| 6,917,865 B2 | 7/2005 | Arai et al. | |
| 6,920,779 B2 | 7/2005 | Carlstom et al. | |
| 7,783,507 B2 | 8/2010 | Schick et al. | |
| 8,131,419 B2 | 3/2012 | Ampunan et al. | |
| 8,359,913 B2 | 1/2013 | Schneider et al. | |
| 9,280,856 B2 * | 3/2016 | Chen | G07C 5/006 |
| 9,388,716 B2 | 7/2016 | Smolenski et al. | |
| 9,415,762 B2 * | 8/2016 | Treharne | F02N 11/0829 |
| 9,444,892 B1 | 9/2016 | Amireddy et al. | |
| 9,714,931 B2 * | 7/2017 | Prabhu | G01N 33/2888 |
| 10,208,638 B2 * | 2/2019 | Wada | F01M 11/10 |
| 2003/0055666 A1 | 3/2003 | Roddy et al. | |
| 2003/0213292 A1 * | 11/2003 | Budeiri | F01M 11/10 73/114.57 |
| 2005/0080606 A1 | 4/2005 | Ampunan et al. | |
| 2006/0005609 A1 * | 1/2006 | Blomkvist | F01M 1/18 73/53.05 |
| 2006/0258377 A1 | 11/2006 | Economos et al. | |
| 2007/0100518 A1 | 5/2007 | Cooper | |
| 2007/0173993 A1 | 7/2007 | Nielsen | |
| 2007/0260374 A1 * | 11/2007 | Morrison | F02D 41/22 701/99 |
| 2008/0039995 A1 | 2/2008 | Reeser | |
| 2008/0154478 A1 * | 6/2008 | Lyons | F01M 1/18 701/102 |
| 2008/0163678 A1 | 7/2008 | Snider et al. | |
| 2010/0152960 A1 | 6/2010 | Huber et al. | |
| 2010/0307230 A1 * | 12/2010 | Gilch | G01N 33/2888 73/114.55 |
| 2011/0208567 A9 | 8/2011 | Roddy et al. | |
| 2012/0042718 A1 * | 2/2012 | Schneider | G01N 33/2888 73/114.55 |
| 2012/0046920 A1 * | 2/2012 | Blossfeld | F01M 1/18 703/2 |
| 2012/0303230 A1 * | 11/2012 | Qiao | G01N 33/1826 701/59 |
| 2013/0287142 A1 | 11/2013 | Geng et al. | |
| 2014/0019068 A1 * | 1/2014 | Schneider | G01N 33/2888 702/30 |
| 2014/0331746 A1 * | 11/2014 | Ito | F01M 11/10 73/53.06 |
| 2014/0365144 A1 * | 12/2014 | Dvorak | G01N 33/2888 702/50 |
| 2015/0192560 A1 * | 7/2015 | Basu | G01N 33/2888 73/114.55 |
| 2015/0338386 A1 * | 11/2015 | Chapman, III | G01N 33/2888 702/50 |
| 2016/0078695 A1 | 3/2016 | McClintic et al. | |
| 2016/0094425 A1 | 3/2016 | Schulz et al. | |
| 2017/0044942 A1 | 2/2017 | Barnickel | |
| 2018/0238433 A1 * | 8/2018 | Syrowik | F01M 11/10 |

OTHER PUBLICATIONS

PCT International Search Report regarding related PCT Application No. PCT/US2018/014139; dated Apr. 26, 2018; 3 pages.
PCT Written Opinion of the International Searching Authority regarding related PCT Application No. PCT/US2018/014139; dated Apr. 26, 2018; 10 pages.

* cited by examiner

Table 1: Field Testing Parameters

| Description | Source | Description | Source |
|---|---|---|---|
| Total Vehicle Distance | ECM | Engine Oil Pressure | ECM |
| Total Fuel Used | ECM | Engine Oil Temperature | ECM |
| Total Engine Time | ECM | Engine Coolant Temperature | ECM |
| Total DEF used | ECM | Ambient Air Temperature | ECM |
| Average Fuel Economy | ECM | Engine Manifold Pressure | ECM |
| Trip Distance | ECM | Engine Manifold Temperature | ECM |
| Trip DEF Usage | ECM | Engine Crankcase Pressure | ECM |
| Trip Fuel | ECM | Engine EGR Temperature | ECM |
| Total Idle Fuel | ECM | DPF Inlet Pressure | ECM |
| Total Idle Time | ECM | DPF Outlet Pressure | ECM |
| Engine Fueling Rate | ECM | SCR Nox Inlet | ECM |
| Vehicle Speed | ECM | SCR Nox Outlet | ECM |
| Total Engine Revolutions | ECM | Engine Exhaust Temperature | ECM |
| Pedal Position | ECM | DPF Pressure Differential | ECM |
| Engine Speed | ECM | Engine Fuel Temp | ECM |
| ECM Percent Load | ECM | | |

FIG.2A

Table 2: Field Testing Parameters

| Description | Source | Description | Source |
|---|---|---|---|
| Engine Torque | Load Cell | Fuel Pressure Supplied to Engine | Transducer |
| Ambient Temp in Test Cell | T/C | Intake Manifold Pressure | Transducer |
| CAC Outlet. Manifold Intel Temp | T/C | Oil Gallery Pressure | Transducer |
| Coolant Temp (in & Out) | T/C | Air Filter Pressure Restriction | Transducer |
| Cylinder #1 - #6 Exhaust Temps | T/C | Turbo Outlet Pressure | Transducer |
| EGR Cooler Gas Temp (in & Out) | T/C | Engine Speed | Spd Pickup |
| Exhaust Gas Temp Downstream | T/C | Pedal Position | ECM |
| Fuel Rail Temperature | T/C | Percent Load | ECM |
| Intake Manifold Temperature | T/C | Idle Fuel Used | ECM |
| Oil Gallery Temperature | T/C | Total Engine Hours | ECM |
| Oil Sump Temp | T/C | Total Fuel Used | ECM |
| Turbo Air (in and Out) | T/C | Engine Coolant Temp | ECM |
| Turbo Exhaust Gas Temp (in and Out) | T/C | Fuel Temp | ECM |
| Boost Pressure | Transducer | Oil Temp | ECM |
| Coolant Pressure | Transducer | Fuel Rate | ECM |
| Crankcase Pressure | Transducer | Boost Pressure | ECM |
| Engine Manifold Pressure (Air) | Transducer | Turbo Oil Temp | ECM |
| Exhaust Back Pressure | Transducer | Engine Percent Torque Output | ECM |

FIG.2B

SYSTEM AND METHOD FOR PREDICTING REMAINING OIL LIFE IN VEHICLES

CROSS REFERENCE TO RELATED APPLICATIONS

The present patent application claims the benefit of U.S. Provisional Patent Application Ser. No. 62/447,545, filed Jan. 18, 2017, the entire contents of which are incorporated by reference herein.

TECHNICAL FIELD

This disclosure generally relates to systems and methods for predicting oil life in vehicles, and more particularly to temperature based predictions of remaining oil life.

BACKGROUND

Motor oil, engine oil, or engine lubricant, generally referred to as oil, is any of various substances comprising base oils enhanced with additives, e.g., anti-wear additive and detergents, dispersants and, for multi-grade oils viscosity index improvers. Lubricating oils can also contain corrosion inhibitors, e.g., rust and oxidation inhibitors. Oil can be used for lubrication of internal combustion engines. The oil reduces friction and wear on moving parts and to clean the engine from sludge (one of the functions of dispersants) and varnish (detergents). The oil can also neutralize acids that originate from fuel and from oxidation of the lubricant (detergents), improves sealing of piston rings, and cool the engine by carrying heat away from moving parts.

SUMMARY

According to some aspects, systems and methods provide for determining a remaining oil life in an engine of a vehicle. At least one parameter of the engine is monitored over a period of time. The parameter includes a hot compartment temperature. A condition of the oil based is determined based on the hot compartment temperature, oil volume, and/or oil formulation. The condition of the oil is then displayed.

Other systems, methods, features, and advantages is or will become apparent upon examination of the following figures and detailed description. It is intended that all such additional systems, methods, features, and advantages be included within this description and be protected by the accompanying claims.

BRIEF DESCRIPTION OF THE DRAWINGS

FIGS. 2A-B include tables of example field testing parameters and engine stand parameters, respectively.

DETAILED DESCRIPTION

The disclosure generally relates to systems and methods for predicting quality and/or remaining usable life of motor oil, engine oil, or engine lubricant, generally referred to herein as oil. In some examples, an oil life determination module determines remaining oil life. In some examples, the oil life determination module reports the remaining oil life remotely, e.g., through telematics, to fleet owners. In some examples, the oil life determination module eliminates a need to actively monitor the oil analysis. In some examples, oil life determinations are used to optimize fleet maintenance options and minimize fleet downtime.

Figure 1:
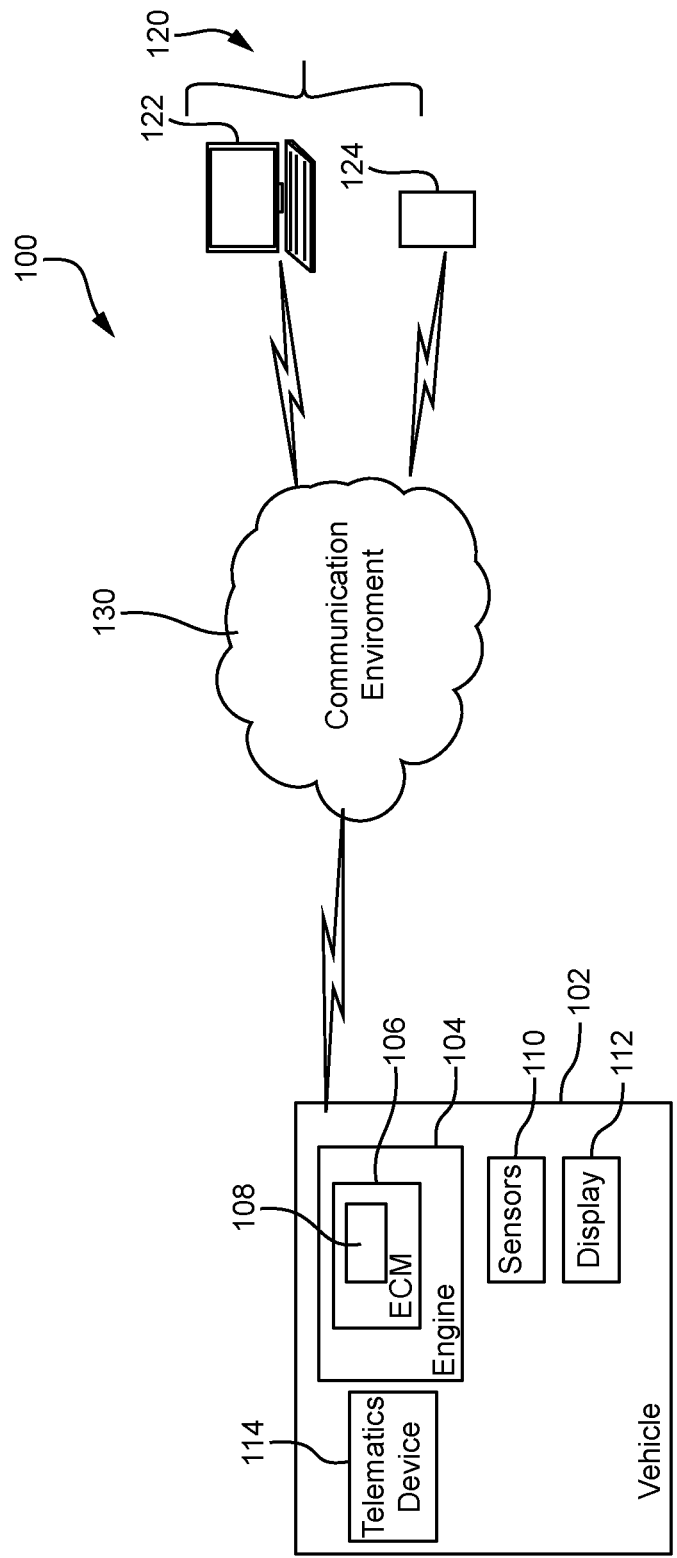
FIG. 1 is a block diagram of an example environment for determining remaining oil life.

FIG. 1 is a block diagram of an example environment 100 for determining remaining oil life in a vehicle 102. The vehicle 102 can include one or more commercial and industrial type vehicles. The vehicle 102 can include one or more of an engine 102, e.g., internal combustion engine, an engine control module (ECM) 106, an oil life determination module 108, sensors 110, one or more displays 112, including audible and/or visual displays, and a telematics device 114. The oil life determination module 108 can be a part of the ECM 106 and/or separate from it. In some examples, the oil life determination module 108 is positioned on the vehicle 102 and/or the oil life determination module 108 is positioned remotely from the vehicle 102. The telematics device 114 provides cellular and/or satellite communication links between vehicle 102 and fleet manager devices 120 remote from the vehicle 102, e.g., via a communication environment 130. The fleet manager devices 120 can include one or more of web portal devices 122 and/or mobile devices 124 for displaying remaining oil life. Mobile devices 124 can include, but are not limited to, smart phones, tablets, personal digital assistants, etc. Web portal devices 122 can include one or more personal computers, laptop computers, etc. In some examples, the mobile devices 124 can act as web portals, e.g., via a web browser of the mobile devices 124. In some examples, the fleet manager devices 120 calculate remaining oil life based on data received from the vehicle 102. In some examples the oil life determination module 108, or parts of it, can be implemented as an app on the mobile devices 124, or an application on the web portal devices 122, for determining and/or displaying the remaining oil life.

The sensors 110 can include, but are not limited to, one or more temperature sensors and pressure sensors for monitoring engine parameters. For real time monitoring and/or field test modeling as used with the oil life determination module 108, in some examples temperature sensors can include ambient air temperature around the engine 104, engine manifold temperature, engine fuel temperature, engine oil temperature, engine coolant temperature, engine exhaust temperature after the exhaust gas re-circulator (EGR) valve, and/or engine exhaust temperature downstream of the EGR, etc. Pressure sensors can include engine manifold pressure, engine crankcase pressure, engine oil pressure, pressure at an inlet to the diesel particulate filter (DPF), pressure at an outlet of the DPF, and/or pressure differential over the DPF, etc. For real time monitoring and/or engine stand modeling as used with the oil life determination module 108 in some examples, temperature sensors can include test cell temperature, fuel pump return temperature, fuel rail temperature, oil gallery temperature, turbo exhaust outlet temperature, EGR gas temperature, exhaust temperature and/or fuel return temperature. Pressure sensors can include oil pressure, e.g., in the sump, fuel pressure to the engine 104, and/or exhaust pressure, e.g., downstream of the EGR, etc. FIGS. 2A-B include tables of example field testing parameters and engine stand parameters, respectively. Other parameters from determining remaining oil life may be used.

In FIG. 1, the communication environment 130 that connects the vehicle 102 with the fleet manager devices 120 can include one or more wired and/or wireless communication mediums, including but not limited to, cellular communications, satellite communications, WiFi, Bluetooth, Ethernet, etc. In some examples, the oil life determination module 108 connects with the telematics device 114 to send determined remaining oil life information, and/or other data, from the vehicle 102 to the fleet manger devices 120, e.g., to be displayed by the fleet manager devices 120. Additionally or alternatively, in some examples, the oil life determination module 108 sends raw data, including but not limited to hot compartment temperature related information, to the fleet manager devices 120, e.g., for the fleet manager devices 120 to determine remaining oil life. Society of Automotive Engineers (SAE) standard J1939 can be used for communication and diagnostics among vehicle components of heavy duty vehicles. In some examples, passenger cars and trucks use the SAE J1979 (On-board diagnostics Parameter IDs) OBDII standard. Other communication protocol standards can be used.

Figure 3:
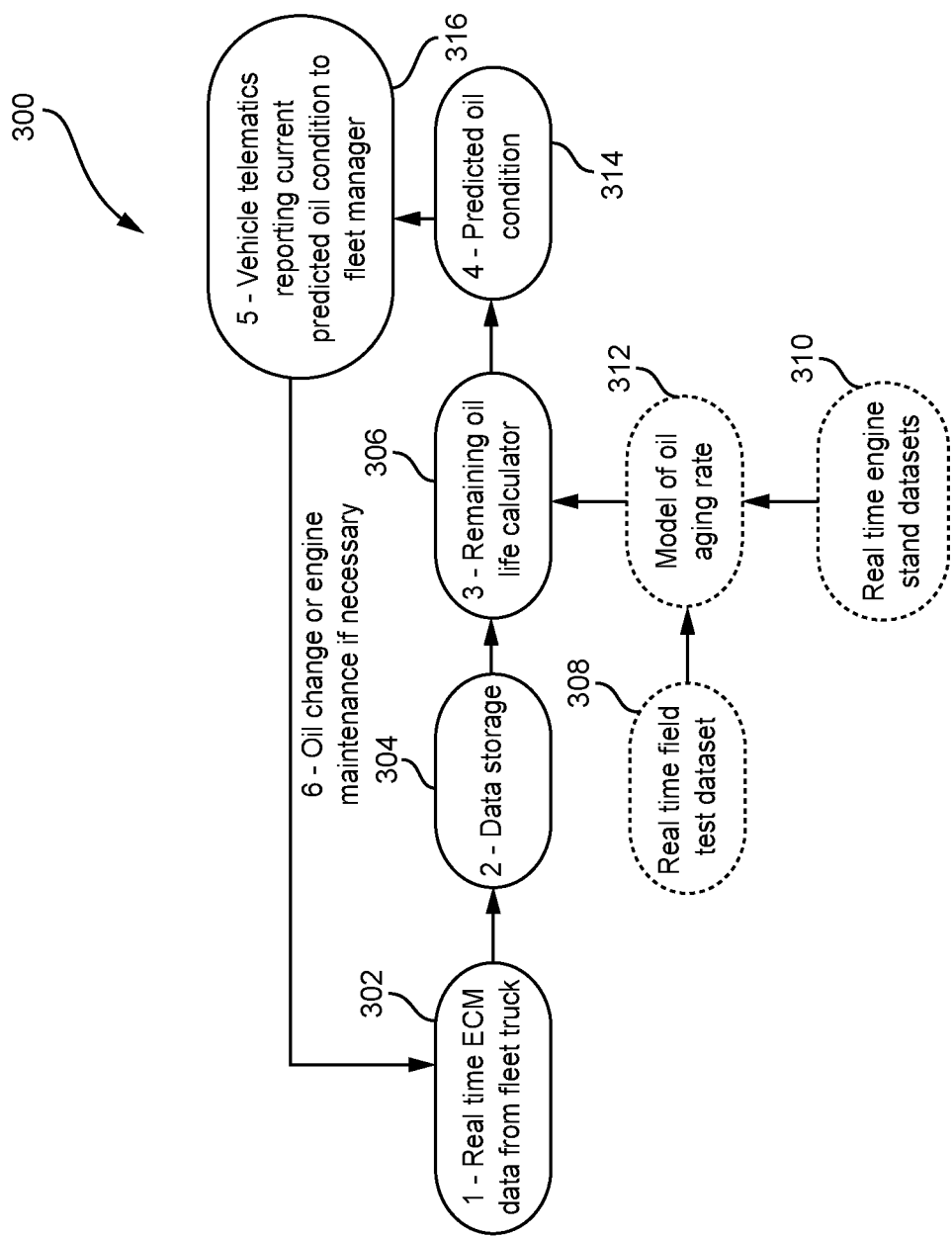
FIG. 3 is a block diagram of an example flow for determining oil performance depreciation.

FIG. 3 is a block diagram of an example flow 300 for determining oil performance depreciation. The ECM 106 can receive real time duty cycle data, temperature data and/or pressure data from the sensors 110, which can be sent to the oil life determination module 108 for determining remaining oil life (302). In some examples, the oil life determination module 108 receives one or more of parameters for determining, e.g., calculating, hot compartment temperatures, bulk temperatures, engine idle time, e.g., total idle time and/or percentage idle time, diesel particulate filter (DPF) pressure differential, percent load, total vehicle distance and/or total engine time, etc. The hot compartment temperatures can be determined from measured parameters, including, but not limited to, piston combustion chamber temperatures, e.g., measured at the exhaust or exhaust related temperatures, which can change more quickly/provide, and include more temperature-based resolution, than the bulk temperatures. The bulk temperatures include oil pan or sump ambient temperature, which may not change as quickly as the determined hot compartment temperatures. The oil life determination module 108 can store the received data for processing (304). The oil life determination module 108 can process the information, e.g., including performing calculations based on the received data, to determine remaining oil life (306).

In some examples, the remaining oil life calculations are based on determined models of oil aging rates 312. Two models are based on, but not limited to, the real time field test datasets 308 and the real time engine stand datasets 310 described above. Using combustion temperatures and other data available from the ECM 106, the oil life determination module 108 determines thermal loading for the vehicle's oil over short increments of time and/or over the long term. By capturing short term events, the oil life determination module 108 can account for localized hot spots which effect small volumes of lubricating oil that are not seen in bulk readings, e.g., short term, high temperature events which occur in the combustion chamber that are not identifiable when looking at bulk oil or coolant temperatures. The short term events can have a large impact on small volumes of oil exposed to very high temperatures, which can shorten oil life. In some examples, the short term, high temperature events are determined for the hot compartment, e.g., the exhaust related temperatures.

The models for oil again rate 312 can include linear and/or non-linear models. The models 312 can be based on real time field test datasets and/or real time engine stand datasets, e.g., as determined based on the engine 104. In some examples, the real time field test datasets and/or real time engine stand datasets can be for determined engine 104 and vehicle 102 implementations. In some examples, the models 312 can include, but are not limited to, differential equation based models, neural network models, linear equation models and/or statistical based models for determining oil aging, e.g., determining a current oil condition/quality and/or remaining life of the oil. In some examples, the oil life determination module 108 can differentiate oil performance categories, e.g., premium products versus conventional products when making the determination. In some examples, a degradation coefficient can be built into the model to account for the differences in oil formulations. As the oil life determination module 108 receives feedback information from the ECM 106 over the oil drain, the oil life determination module 108 can update the models to account for oxidation rates, providing a real time look at oil health and determined future performance.

Based on one or more of the determined hot compartment temperatures, other received duty cycle information, temperature and/or pressure data, oil volume, oil formulation, and/or the model of oil aging rates 312, the oil life determination module 108 can determine remaining oil life for the vehicle 102 (314). Determined remaining oil life, e.g., based on oil use limits, can dictate when it is time to discard and replace the oil. The display 112 can display remaining oil life in the vehicle 102 and/or the vehicle 102 can report the remaining oil life to fleet manager devices 120, e.g., via the telematics device 114 (316). Based on the displayed remaining oil life the oil can be replaced.

Figure 4:
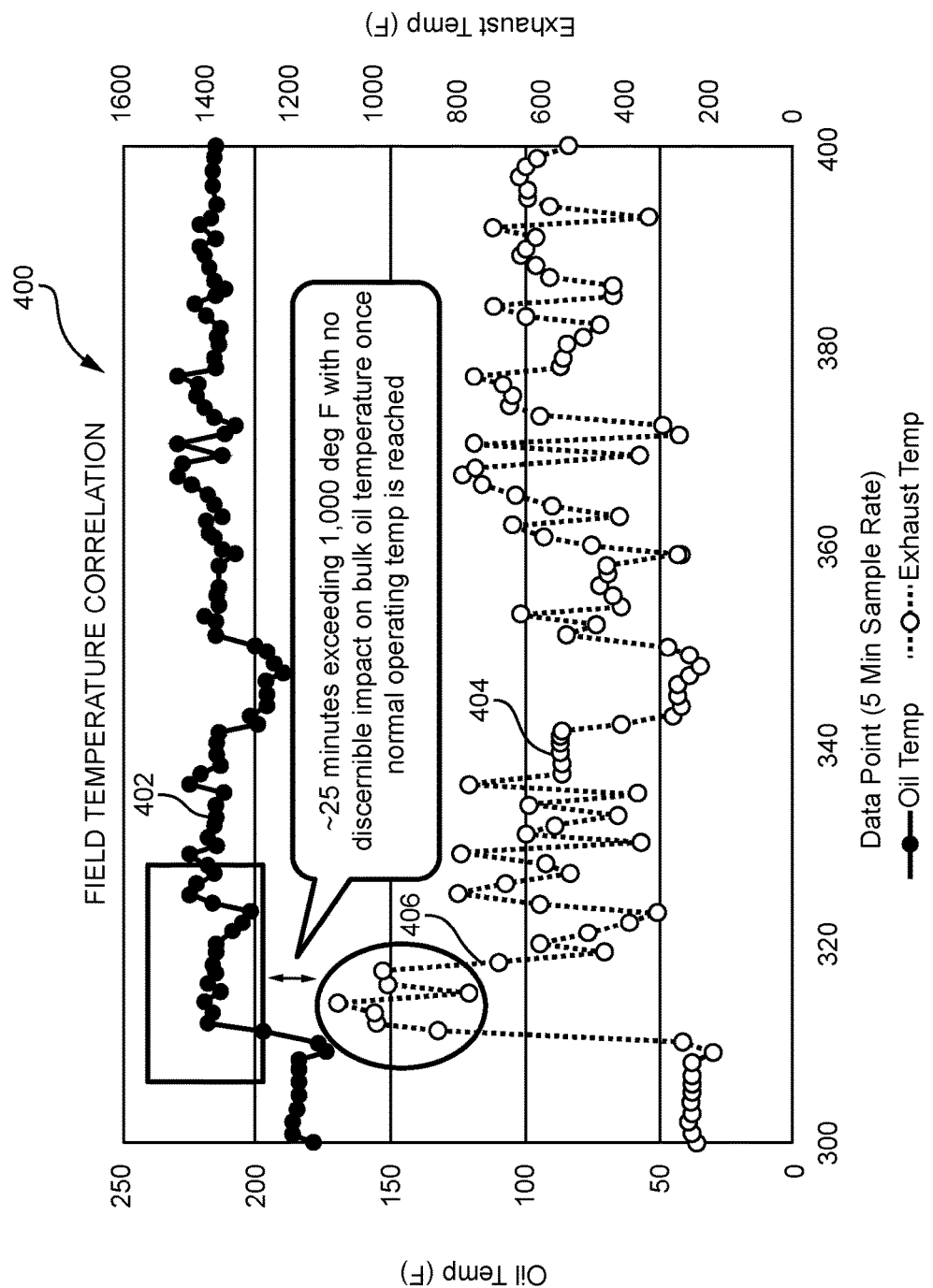
FIG. 4 is a graph of an example temperature correlation between exhaust temperature and oil temperature.

FIG. 4 is a graph 400 of an example temperature correlation between exhaust temperature and oil temperature. In this example, while the exhaust temperature 402 exceeds 1000 degrees Fahrenheit for twenty-five minutes, there is no discernible impact on bulk oil temperature 404 once normal operating temperature 406 is reached. Therefore, in some examples, the oil life determination module 108 uses determined hot compartment temperatures, alone or in combination with bulk temperatures, when determining a remaining oil life.

In some examples, the oil life determination module 108 can determine a remaining oil life used in internal combustion engines 104 of vehicles 102. The oil life determination module 108 can receive ECM parameters over a period of time, e.g., starting when new oil is added to the engine 104. The newly added oil can be detected by an oil level sensor that is telemetrically monitored, e.g., over a telematics communication link. The oil level can be detected and reported after engine 104 shutdown on each trip, e.g., once vehicle levelness has been verified by on-board sensors. From the received parameters, the oil life determination module 108 can determine a current quality of the oil and/or useful life of the oil based on the engine parameters. At least one of the parameters can include exhaust temperature, e.g., measured directly and/or determined from based on other parameters including those described herein. In some examples, the oil life determination module 108 can factor in empirically determined oil deterioration factors, e.g., based on oil. The oil life determination module 108 can also factor in real-time data previously obtained from testing performance characteristics of a same make of engine 104 as in the vehicle 102. In some examples, the vehicle 102 can telemetrically conveying the current quality of oil to a remote party, e.g., via fleet manager devices 120. The fleet manager devices 120 can determine when to schedule an oil change based on the telemetrically conveyed current quality of oil.

Figure 5:
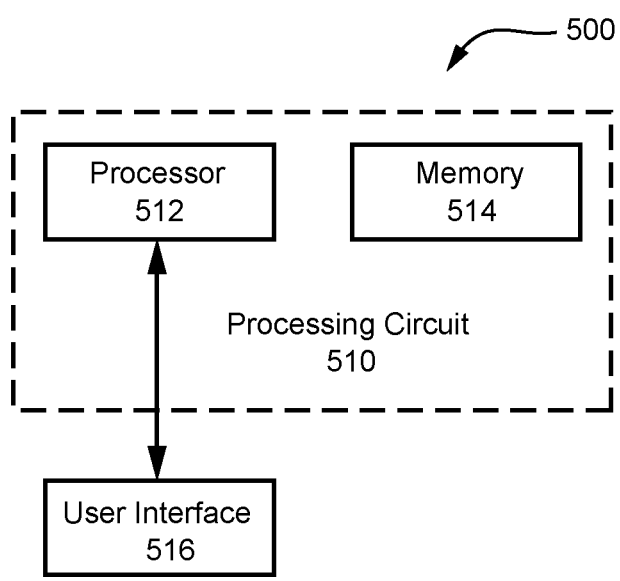
FIG. 5 is a block diagram of an example computing device.

FIG. 5 is a block diagram of an example circuitry, e.g., for one or more of the ECM 106, the web portal device 122 and the mobile device 124. The ECM 106, the web portal device 122 and/or the mobile device 124 can include a processing circuit 510 which includes a processor 512 to process the inputs from the engine sensors 110, e.g., in real-time. For example, the processor 512 of the ECM 106 can process the inputs from the engine sensors 110, e.g., in real-time. The processing circuit 510 can include hardware, software and/or firmware, or any combination thereof. The hardware can include electronic components on a printed circuit board, ceramic substrate or a thin laminate substrate, etc. Software can be stored in a memory 514, e.g., erasable, programmable read only memory (EPROMs) or flash memory, so the processor 512 can be re-programmed by uploading updated code or replacing chips. It will be appreciated that the components, devices or elements illustrated in and described with respect to FIG. 5 may not be mandatory and thus some may be omitted in certain examples. Additionally, some examples may include further or different components, devices or elements beyond those illustrated in and described with respect to FIG. 5.

In some examples, the processing circuitry 510 is configurable to perform actions in accordance with one or more examples disclosed herein. In this regard, the processing circuitry 510 may be configured to determine oil life. The processing circuitry 510 may be configured to perform data processing, application execution and/or other processing and management services according to one or more examples. In some examples, the processing circuitry 510 or a portion(s) or component(s) thereof, may include one or more chipsets and/or other components that may be provided by integrated circuits.

The processor 512 may be embodied in a variety of forms. For example, the processor 512 may be embodied as various hardware-based processing means such as a microprocessor, a coprocessor, a controller or various other computing or processing devices including integrated circuits such as, for example, an ASIC (application specific integrated circuit), an FPGA (field programmable gate array), some combination thereof, or the like. Although illustrated as a single processor, it will be appreciated that the processor 512 may comprise a plurality of processors. The plurality of processors may be in operative communication with each other and may be collectively configured to perform one or more functionalities of the ECM 106, the web portal device 122 and the mobile device 124 as described herein. In some examples, the processor 512 may be configured to execute instructions that may be stored in the memory 514 or that may be otherwise accessible to the processor 512. As such, whether configured by hardware or by a combination of hardware and software, the processor 512 is capable of performing operations according to various examples while configured accordingly.

In some examples, the memory 514 may include one or more memory devices. Memory 514 may include fixed and/or removable memory devices. In some examples, the memory 514 may provide a non-transitory computer-readable storage medium that may store computer program instructions that may be executed by the processor 512. In this regard, the memory 514 may be configured to store information, data, applications, instructions and/or the like for enabling the ECM 106, the web portal device 122 and/or the mobile device 124 to carry out various functions in accordance with one or more examples. In some examples, the memory 514 may be in communication with one or more of the processor 512, the user interface 516 for passing information among components of the ECM 106, the web portal device 122 and the mobile device 124.

It is noted that the terms "substantially" and "about" may be utilized herein to represent an inherent degree of uncertainty that can be attributed to any quantitative comparison, value, measurement, or other representation. These terms are also utilized herein to represent a degree by which a quantitative representation may vary from a stated reference without resulting in a change in the basic function of the subject matter at issue.

While particular examples above have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for predicting a remaining oil life in an engine of a vehicle, comprising:
   monitoring at least one parameter of the engine over a period of time, wherein the at least one parameter comprises at least a total idle time;
   determining a hot compartment temperature from the parameter;
   determining a condition of the oil based on the hot compartment temperature; and
   displaying the condition of the oil.

2. The method of claim 1, further comprising starting the monitoring when new oil is added to the engine.

3. The method of claim 1, where the determining further comprise factoring in real-time data previously obtained from testing performance characteristics of a same make of engine as in the vehicle.

4. The method of claim 1, where the at least one parameter for determining hot compartment temperature comprises at least one of an exhaust temperature and exhaust related temperature.

5. The method of claim 1, further comprising telemetrically conveying a condition of oil to a remote party.

6. The method of claim 5, further comprising determining when to schedule an oil change based on the telemetrically conveyed condition of oil.

7. The method of claim 1, further comprising sending the at least one parameters from an engine control module.

8. The method of claim 1, where the at least one parameter further comprises a duty cycle of the engine.

9. The method of claim 1, where the determining is further based on a previously determined model.

10. The method of claim 9, where the previously determined model comprises a field test model and an engine stand model.

11. The method of claim 10, where the determining further includes an empirically determined oil deterioration factor.

12. A system for determining a remaining oil life in an engine of a vehicle, comprising:
   an electronic control module configured to monitor at least two parameters of the engine over a period of time, where the at least two parameters include a total idle time and a hot compartment temperature; and an oil life determination module configured to determine a condition of the oil based on the total idle time and the hot compartment temperature and display the condition of the oil.

13. The system of claim 12, where the oil life determination module is configured to determine the condition based on when new oil is added to the engine.

14. The system of claim 13, further including an oil level sensor, where new added is determined by the oil level sensor.

15. The system of claim 12, where the oil life determination module is configured to determine the condition based on real-time data previously obtained from testing performance characteristics of a same make of engine as in the vehicle.

16. The system of claim 12, where the hot compartment temperature comprises is determined from an exhaust temperature.

17. The system of claim 12, further comprising a telematics device, where the telematics device is configured to telemetrically convey a condition of oil to a fleet manager device.

18. The system of claim 17, where the fleet manager device is configured to schedule an oil change based on the telemetrically conveyed condition of oil.

19. The system of claim 12, where the parameter further comprises a duty cycle of the engine.

20. The system of claim 12, where the oil life determination module is configured to determine the condition based on a previously determined model.

21. The system of claim 12, where a previously determined model comprises a field test model and an engine stand model.

22. The system of claim 12, where the oil life determination module is further configured to determine the condition based on an empirically determined oil deterioration factor.

* * * * *